(12) United States Patent
Nordberg et al.

(10) Patent No.: US 8,496,820 B2
(45) Date of Patent: Jul. 30, 2013

(54) METHOD AND APPARATUS FOR FORMING AN HOMOGENEOUS MIXTURE OF CHROMATOGRAPHY MEDIA IN A VESSEL

(75) Inventors: Roger Nordberg, Uppsala (SE); Alan M. Williams, Easton, PA (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 139 days.

(21) Appl. No.: 12/608,027

(22) Filed: Oct. 29, 2009

(65) Prior Publication Data

US 2010/0046322 A1 Feb. 25, 2010

Related U.S. Application Data

(62) Division of application No. 11/669,347, filed on Jan. 31, 2007.

(51) Int. Cl.
*B01D 15/08* (2006.01)
*G01N 30/02* (2006.01)

(52) U.S. Cl.
USPC .......... 210/198.2; 210/656; 422/68.1; 422/70

(58) Field of Classification Search
None
See application file for complete search history.

(56) References Cited

U.S. PATENT DOCUMENTS

| | | | |
|---|---|---|---|
| 5,676,837 | A | 10/1997 | Jungbauer et al. |
| 6,117,317 | A | 9/2000 | Dickson et al. |
| 6,802,638 | B2 | 10/2004 | Allen |
| 2003/0098280 | A1 | 5/2003 | Davis et al. |

FOREIGN PATENT DOCUMENTS

| | | |
|---|---|---|
| GB | 2344543 | 6/2000 |
| WO | WO02/10739 | 2/2002 |

*Primary Examiner* — Katherine Zalasky

(57) ABSTRACT

The present invention relates to methods and apparatus for forming an homogeneous mixture of chromatography media in a vessel. The invention also relates to methods and apparatus for transferring the homogeneous media from the vessel into a second vessel in preparation for packing a chromatography column. The invention can also be used directly to pack the column with homogeneous media.

11 Claims, 6 Drawing Sheets

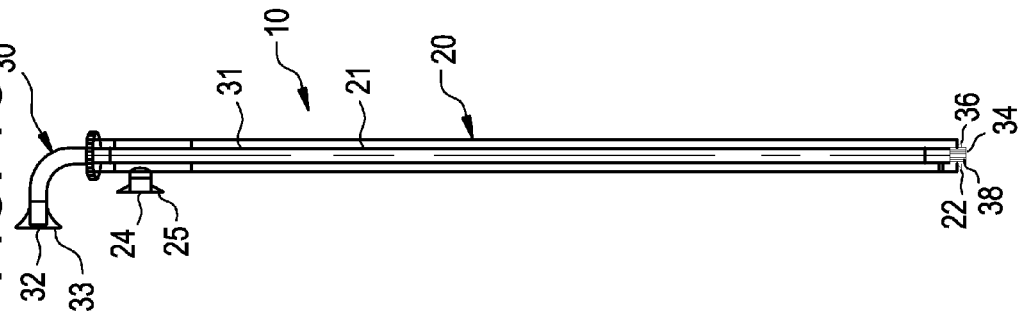
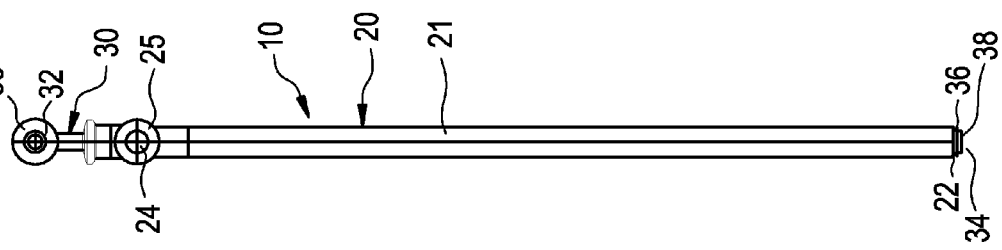
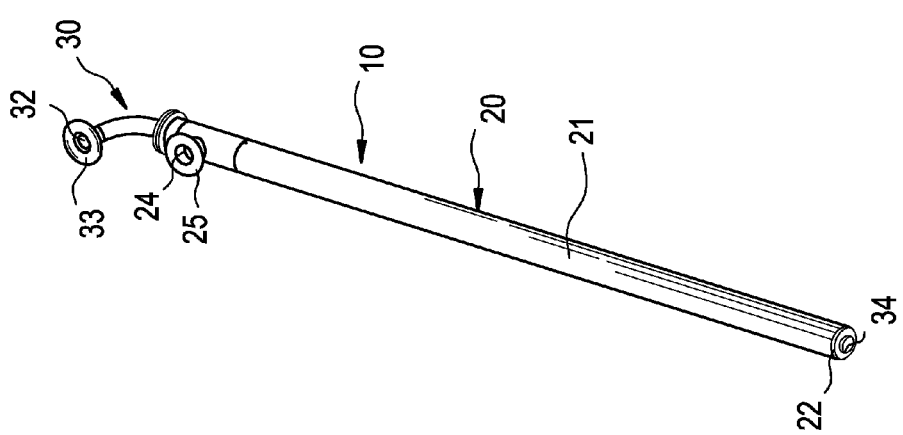

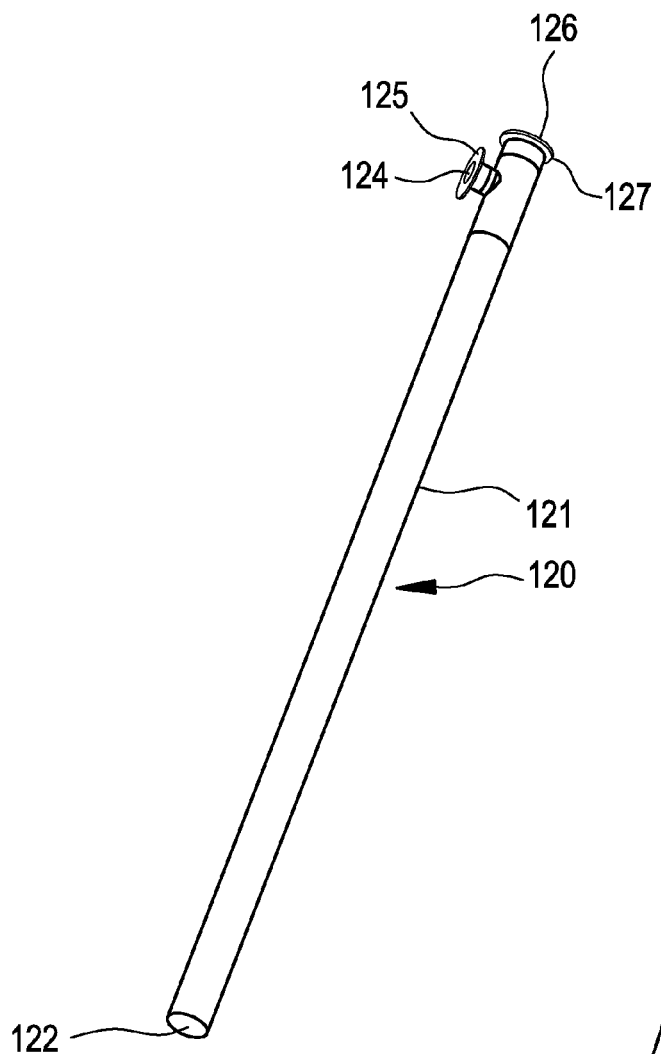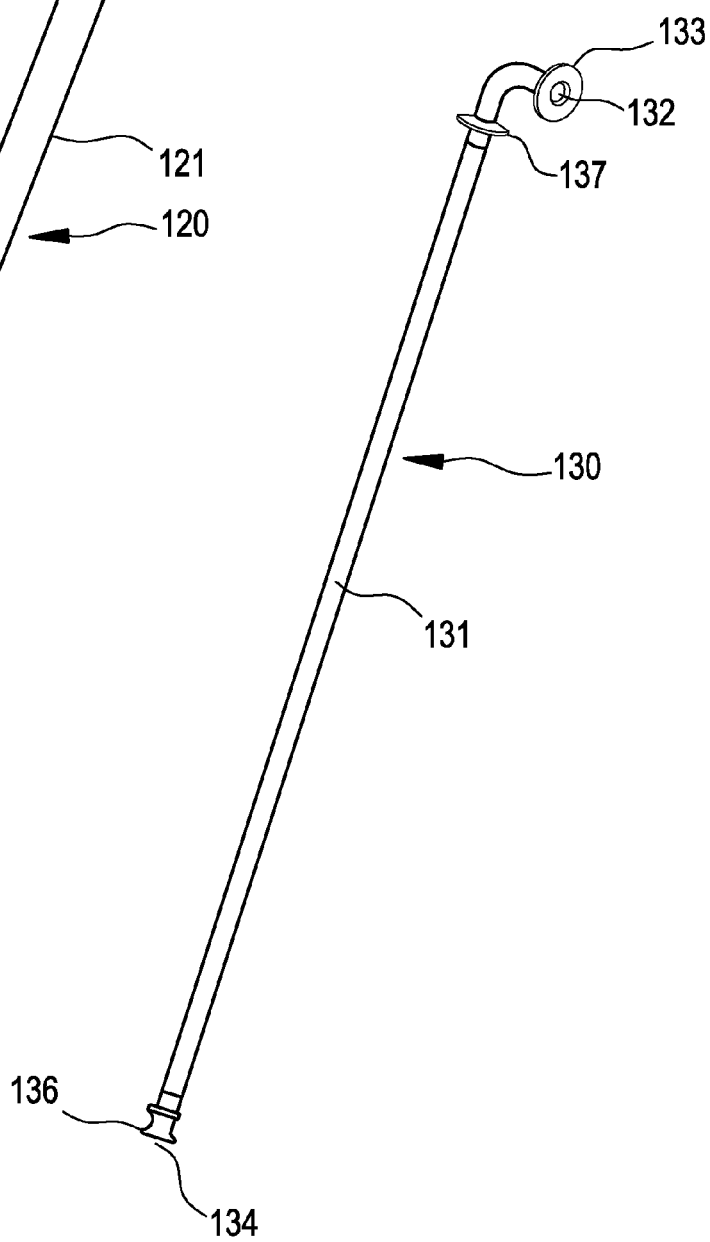

METHOD AND APPARATUS FOR FORMING AN HOMOGENEOUS MIXTURE OF CHROMATOGRAPHY MEDIA IN A VESSEL

CROSS-REFERENCE TO RELATED APPLICATIONS

This application is a divisional of U.S. patent application Ser. No. 11/669,347 filed Jan. 31, 2007.

FIELD OF THE INVENTION

The present invention relates to methods and apparatus for forming a homogeneous mixture of chromatography media in a vessel and for transferring the mixture to another vessel or directly to a chromatography column.

BACKGROUND OF THE INVENTION

Chromatography is a well-established and valuable technique for separating chemical and biological substances and is widely used in research and industry, finding many applications in compound preparation, purification and analysis. There are many different forms of chromatography, liquid chromatography being of particular importance in the pharmaceutical and biological industries for the preparation, purification and analysis of proteins, peptides and nucleic acids.

Columns used in liquid chromatography typically comprise a tubular body enclosing a porous chromatography medium through which a carrier liquid flows, with separation taking place by material collection between the carrier liquid and solid phase of the porous medium. Prior to any separation process, the bed has to be prepared starting from the slurry of particles that has to be introduced into the column. The packed bed is formed by consolidating a suspension of discrete particles, known as "slurry" that is pumped or poured or sucked into the column, usually from one end. The end piece or net allows liquid to flow from the column whilst retaining the porous material and consolidates the particle from the slurry inside the column.

The size of columns varies depending upon the scale of separation which is required. Thus, for example, research laboratories may only require columns which hold relatively small volumes of chromatography media, typically of the order of 100 µl to 1 L. In contrast, industrial laboratories which handle high volumes of samples which require purification or preparation, often require columns with much greater capacities, typically well in excess of 5 L and often in the 50 L to 1000 L range.

There are many different forms of chromatographic media used for separating, purifying and analysing chemicals such as proteins, peptides and nucleic acids. For example, some media effect separation on the basis of size while others utilise charge and/or affinity to separate the analyte of interest.

Chromatographic media which is to be used for packing industrial columns is often stored and transported in large containers to industrial laboratories. These containers, which can be made of any suitable inert material such as plastic or metal, typically hold in excess of 5 L of chromatography media and are heavy and difficult to manipulate, particularly the larger containers which hold 50 L-100 L of media. Due to their bulk and weight, the containers are generally transported from suppliers to industrial laboratories on pallets to facilitate mechanical handling. In order to prevent or minimise microbiological contamination, the media is often stored in an alcoholic or bacteriostatic solution until such time as it is to be used for packing columns. The media tends to settle out on storage such that it is covered by a supernatant of the alcoholic or bacteriostatic solution.

Once the container reaches the industrial laboratory, it may be kept in storage until such time as the media is required for packing chromatography columns. In order to use the media for packing such columns, the supernatant is usually removed by siphoning or decanting as the alcoholic supernatant would impinge on both environmental and safety concerns in the laboratory facility. A suitable buffer or water is added to the container to make up the volume of storage solution removed and is then used to re-suspend the media. A homogeneous mixture of the re-suspended media is then produced by either manually shaking the containers, stirring them with a paddle or physically removing them from the carrier, such as a pallet, and manually rolling them across the floor. The resulting media must then be decanted or siphoned from these containers to another vessel for subsequent mixing with an appropriate concentration of a suitable buffer prior to packing the chromatography column.

Many problems are encountered in the above described process which are predominantly due to the size and weight of the containers. Decanting the supernatant manually from the containers can lead to a loss of expensive media. The preparation of an homogeneous mixture of media in the container by manually shaking or rolling the container is a time consuming and arduous task which requires considerable strength and dexterity of the operator. This procedure can pose safety risks to the operator in removing the heavy containers from the pallet to roll them in order to mix the media this is also a time consuming process. The mixed media must be continuously agitated or stirred in order to prevent it settling out on standing. Furthermore, problems also arise in transferring the media to a second vessel to form a final slurry for packing the column because media may be lost in siphoning or decanting it from the drum due to adhesion to the walls of the container or spillage. Additional problems may be encountered in diluting the media to a predetermined concentration (typically greater than 50% weight/volume) for use in packing a chromatography column.

The present invention addresses the aforementioned problems and presents methods, apparatus and systems for overcoming and resolving these technical difficulties. It is an object of the invention to provide an improved and more efficient method for forming a homogeneous mixture of chromatography media of all types in most typical containers and for transferring the mixture to a second vessel, such as a slurry tank, or to a chromatography column for packing. A further object of the invention is to provide apparatus and systems with which to carry out the improved method of the invention.

SUMMARY OF THE INVENTION

In accordance with a first aspect of the invention, there is provided a method for forming a homogeneous mixture of chromatographic media in a vessel; said media being present in a first liquid comprising a supernatant, the method comprising the steps of:
(a) removing said supernatant from said vessel by aspirating the supernatant through a tubular member;
(b) discarding the supernatant as waste;
(c) adding a second liquid to the media in the vessel with said tubular member to form a slurry therein;
(d) aspirating said slurry from the vessel through the tubular member; and (e) adding the slurry back into the vessel through the tubular member to form said homogeneous mixture of chromatographic media.

In a second aspect of the present invention, there is provided computer software arranged to carry out the method as hereinbefore described.

In a third aspect of the present invention, there is provided a data carrier storing the computer software as hereinbefore described.

According to a fourth aspect of the present invention, there is provided an apparatus for forming a homogeneous mixture of chromatographic media in a vessel containing said media, the apparatus comprising: a tubular member, said member comprising a first tube and a second tube wherein,
(a) said first tube comprises an elongate body having a first orifice for entry of liquid or slurry therein and a second orifice for exit of liquid/supernatant or slurry therefrom; and
(b) said second tube comprising an elongate body having a first port for entry of liquid or slurry therein and a second port for exit of liquid or slurry therefrom.

In accordance with a fifth aspect of the present invention, there is provided a system for forming an homogeneous mixture of chromatographic media in a vessel containing said media in accordance with the method described hereinbefore, said system comprising an apparatus as described hereinbefore attached to a pump.

BRIEF DESCRIPTION OF THE DRAWINGS

FIG. 1(a) is a three dimensional schematic representation of a tubular member in the form of a hand held rod in accordance with the invention.

FIG. 1(b) is a front view of the tubular member of FIG. 1(a).

FIG. 1(c) is a sectional view of the tubular member of FIG. 1(b).

FIG. 2(a) is a perspective view of a first tube according to the invention.

FIG. 2(b) is a perspective view of a second tube according to the invention.

DETAILED DESCRIPTION OF THE INVENTION

Figure 3:
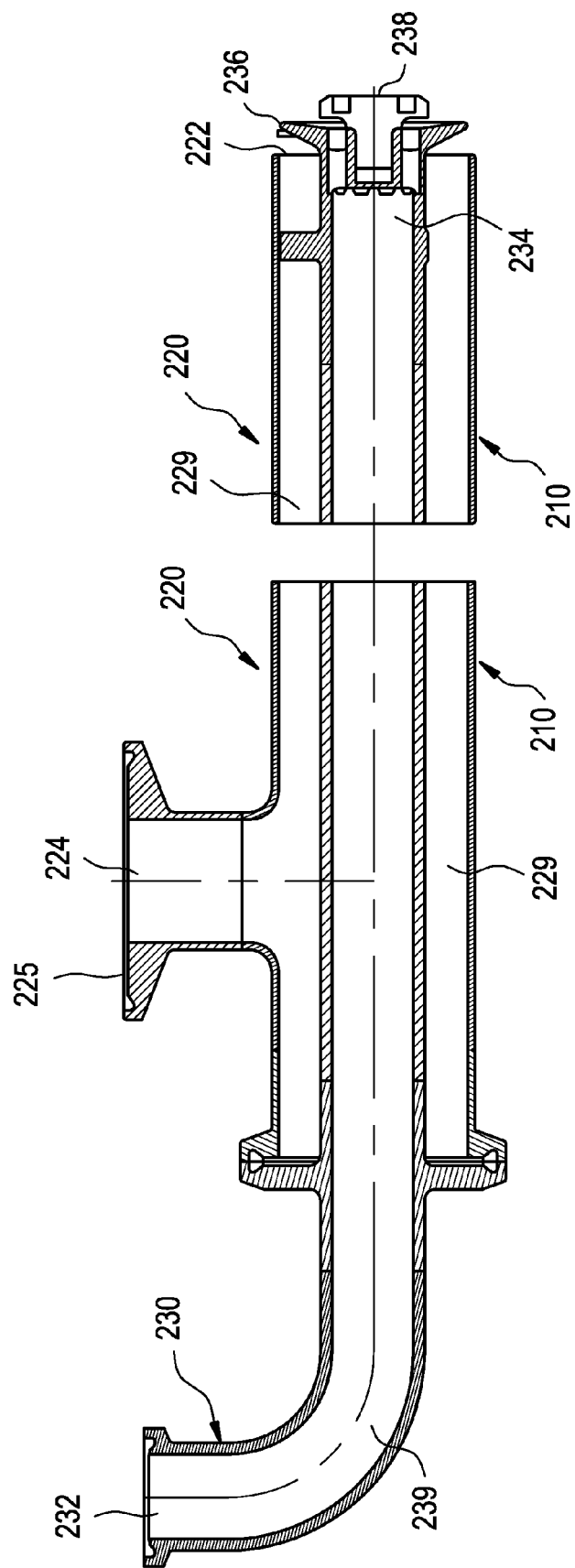
FIG. 3 is detailed cross-sectional view of either end of the tubular member of FIG. 1(a).

The numbering used in FIGS. 1(a), (b) and (c) refer to the same features of the tubular member (10). FIG. 1(a) is a three dimensional representation of a tubular member (10), in the form of a hand held rod, in accordance with the invention. The tubular member (10) comprises a first tube (20) or outer tube and a second tube (30) or inner tube, both outer tube (20) and inner tube (30) having an elongate body (21, 31—FIG. 1(c)). The outer tube (20) is concentric with respect to the inner tube (30). The inner tube (30) comprises a first port (32) which allows entry of a liquid or slurry into the body of the tube (30) and a second port (34) where the liquid or slurry exits the tube (30). The first port (32) can be connected by means of hosing (not shown) attached to adapter (33) to a pump (not shown) which is in fluid communication with a reservoir containing liquid, buffer or slurry. The second port (34) is provided with a nozzle (36—FIGS. 1(b) and (c)) and an end piece (38—FIGS. 1(b) and (c)) for spraying liquid, such as buffer, water or media slurry from the inner tube (30). The angle between the end piece (38) and the nozzle (36) controls the direction of the spray of the liquid exiting from the second port (34) of the inner tube (30), the angle being configured to prevent liquid being aspirated into the first orifice (22) of outer tube (30). Preferably the nozzle produces a radial spray of liquid or slurry directed at an angle of at least 90 degrees to the elongate body of the outer tube (20).

The first tube (20) or outer tube of the tubular member (10) enclosing the inner tube (30) comprises a first orifice (22) through which liquid or slurry is drawn or aspirated into the body of the tube (20) and a second orifice (24) through which liquid, such as a supernatant, or slurry exits the tube (20). Liquid or slurry is drawn into the body of the outer tube (20) at first orifice (22) by means of a vacuum created by a pump (not shown) connected through appropriate hosing (not shown) to the second orifice via adapter (25). The liquid or slurry is then aspirated through the lumen or bore of the elongate body (21) of the first tube (20) member to exit at second orifice (24).

Both the outer tube (20) and the inner tube (30) are predominantly fabricated from a biologically inert material such that it does not elicit an immune response in humans in accordance with United States Pharmacopia (USP) <88> class V1, such as polypropylene, TEFLON™ or stainless steel. The nozzle (36) and end piece (38) being made of an appropriate plastic such as polypropylene or TEFLON™.

FIG. 1(b) shows a front view of the tubular member (10) of FIG. 1(a). The second or inner tube (30) is largely enclosed by the first or outer tube (20). Hosing or suitable piping (such as pressure piping; not shown) connects the second orifice (24) and first port (32) to a pump (not shown) by means of adapters (25, 33). One end of the elongate body (31) of the second or inner tube (30) comprises a nozzle (36) and end piece (34), as described for FIG. 1(a) above. The pump can aspirate or draw liquid into the body of the first/outer tube (20) through the first orifice (22) of the outer tube (20), specifically through the gap between the nozzle (36) and end of the tube (20) (see also FIG. 3).

FIG. 1(c) is a sectional side view of the tubular member (10) showing the concentric configuration of the first (20) and second (20) tubes about the central axis of the member (10). Adapters (25, 33) at orifice/port (24, 32) are suitable for affixing to hosing or piping which is connected to a pump in order to aspirate liquid through the first orifice (22) in the outer tube (20) or spray liquid from the nozzle (36) of the second port (34).

In the embodiment shown in FIGS. 1(a), (b) and (c) the tubular member (10) is assembled as one unit; however, while the member may be fabricated as one integral unit it may also be designed such that it can be separated into its component parts of first (20) and second (30) tubes in order to facilitate cleaning, as illustrated in FIGS. 2(a) and (b). FIG. 2(a) shows a perspective view of first tube (120) having an elongate body (121) with a first orifice (122) at one end of the tube (120), which allows entry of liquid or slurry into the interior of the tube (120), and a second orifice (124) for exit of liquid or slurry from the interior of the tube (120) proximal the second end of the tube. The tube (120) can be connected to a pump by means of suitable pressure piping or hosing which affixes to adapter (125) around the second orifice (124). A third orifice (126) is dimensioned to allow insertion of the second tube (130) into the interior of the first tube (120). The second tube (130), as can be seen in FIG. 2(b), is of narrower bore to the first tube (120) and comprises an elongate body (131) having a first port (132) and a second port (134) at either end from which liquid or slurry can enter and exit the tube (130), respectively. Pressure hosing or piping (not shown) can be affixed to adapter (133) around first port (132) in order to drive the spray of liquid or slurry through the tube to exit from second port (134) via nozzle (136).

The tubular member is assembled by inserting the nozzle (136) of second tube (130) through the third orifice (126) of first tube (120) and feeding the elongate body of the tube (130) through the first tube (120) until the sealing rings (127, 137) of the respective tubes (120, 130) make a fluid-tight seal. The tubes (120, 130) are then in a concentric relationship. The first (120) and second (130) tubes may then be locked into position by means of a releasable fixture such as a locking ring (not shown).

FIG. 3 is a cross-sectional view detailing either end of tubular member (210) which comprises a first or outer tube (220) and a second or inner tube (230). As can be seen from the figure, end piece (238) is positioned within the second port (234) of the second or inner tube (230) adjacent to nozzle (236). Liquid or slurry entering the inner bore or lumen (229) through first orifice (222) of first tube (220) must do so between the gap between the nozzle (236) and the end of the first tube (220). The liquid or slurry is drawn into the lumen (229) or bore of the tube (220) by means of a vacuum which is produced by connecting the first tube (220) to a pump (not shown) at second orifice (224). The connection is achieved by affixing hosing or piping between the pump and around second orifice (224) using adapter (225). Slurry or liquid is aspirated through the lumen or bore (229) of the tube (220) and out of the second orifice (224); the aspirated fluid can be discarded as waste (e.g. in the case of a supernatant), re-circulated back into the second tube (230) to facilitate mixing or, when mixing is complete, directed to a chromatography column or to a slurry tank in readiness for column packing. The distribution of the liquid or slurry will be controlled by means of suitable valves and pumps.

Liquid, such as buffer, which is to be added to the vessel containing the chromatography media is pumped from an appropriate reservoir (not shown) through first port (232) and lumen (239) along the length of the tube (230) and sprayed through second port (234) and nozzle (236) into the vessel. Alternatively, slurry which has already been aspirated from the vessel through the first or outer tube (220), as described above, is then re-circulated through the second or inner tube (230) and spayed back into the vessel under pressure from the pump. This continuous process of aspiration into and through the first tube (220), along the length of the hosing or piping, and then pressurised spaying of the slurry back into the vessel forms a homogeneous mixture of chromatography media. The media can be sprayed into the vessel with sufficient force to break up any aggregates of media which have formed on storage. Typically, a pressure of 2-5 bar is sufficient. After a few cycles of this process, the media is sufficiently mixed that it can be transferred to another vessel or used to pack a chromatography column. Using a pressure of 2-5 bar the entire mixing and cycle time to produce an homogeneous mixture of chromatographic media ready for packing a column will be typically be of the order of 2 to 10 minutes. This is much faster, safer and convenient than using conventional shaking, rolling and siphoning techniques.

Figure 4:
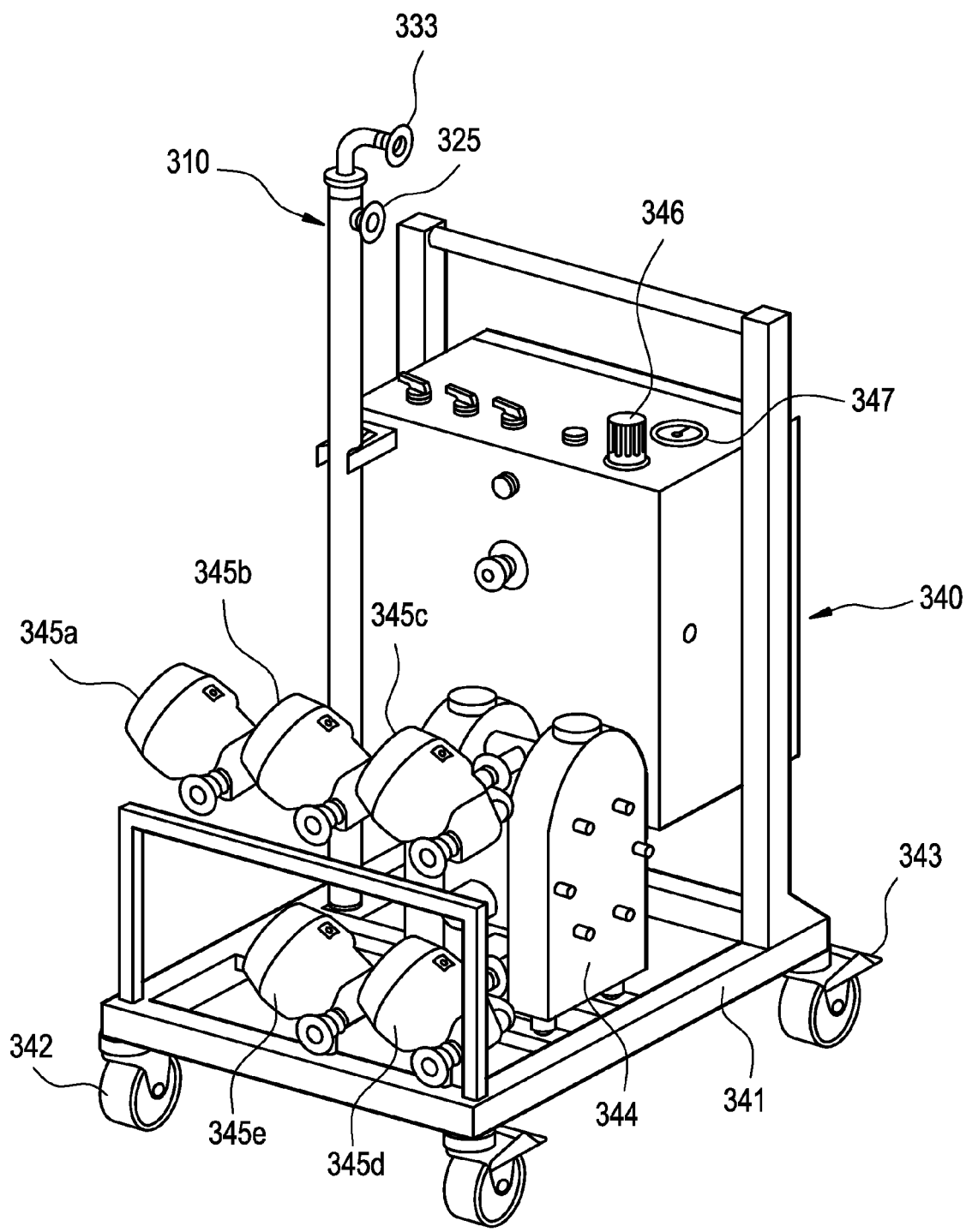
FIG. 4 is a perspective view of a tubular member in accordance with the invention attached to a mobile pump skid.

FIG. 4 is a perspective view of a tubular member (310) in accordance with the invention attached to a mobile pump skid (340). The pump skid (340) is supported on a movable trolley (341) with wheels (342), each having a brake (342) and a handle to facilitate movement. In the embodiment shown, the pneumatic pump unit (344) has five valves (345a-c) which govern the flow of liquid to/from the pump and media container. It will be understood that the method of the invention can be carried out with varying numbers of valves, typically with at least three valves. Each valve can be independently controlled by the operator. A regulator (346) governs the operating pressure which can be monitored on pressure gauge (347). The pressure hosing or piping connecting the tubular member to the pump (at adapters 325 and 333) is not shown in the diagram. The pump may be powered by electricity or by any suitable energy source.

Figure 5:
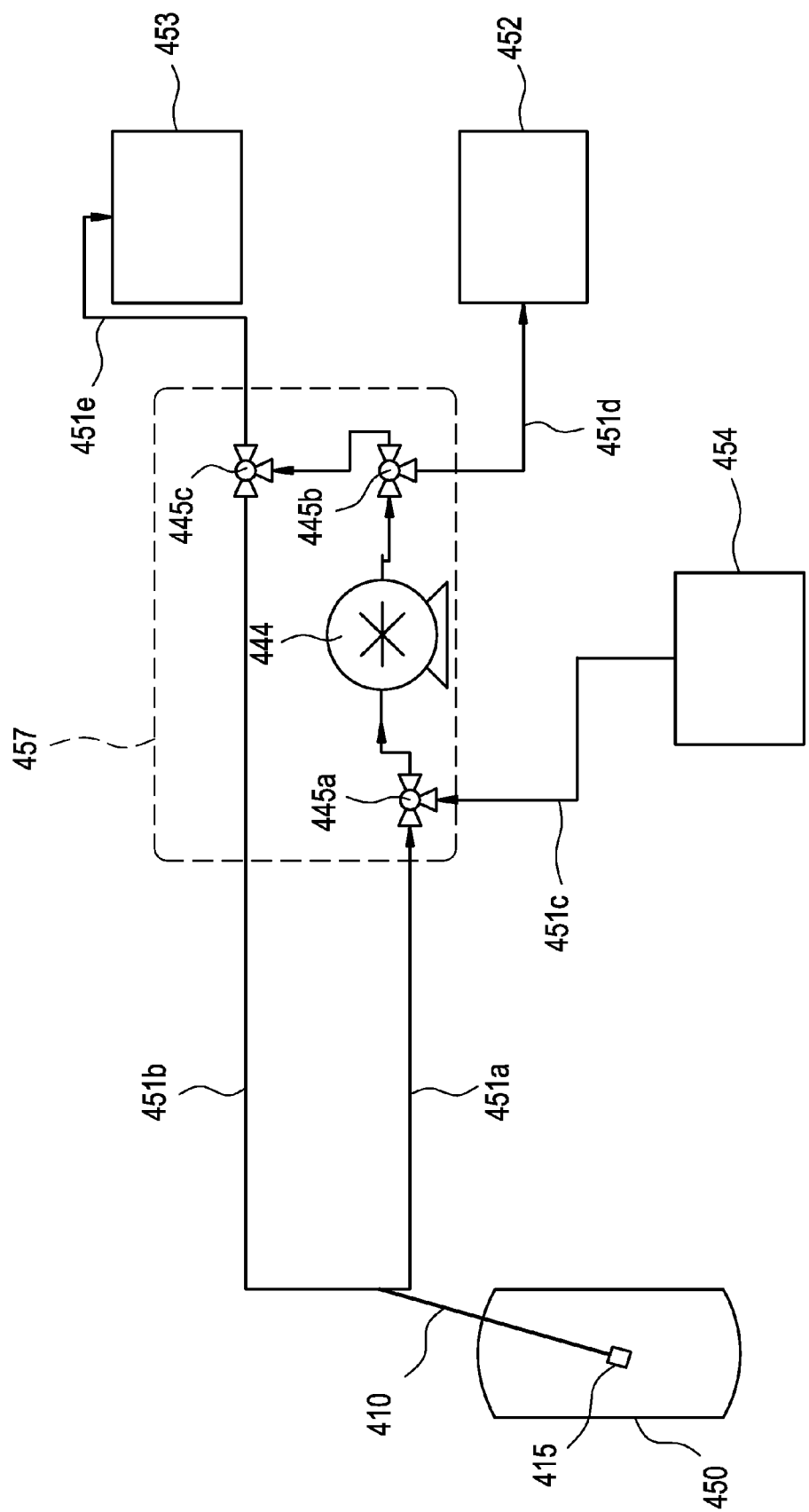
FIG. 5 is a diagram illustrating a system in accordance with the invention.

FIG. 5 is a diagram illustrating a system for carrying out the method of the invention using a tubular member according to the invention attached to a suitable pump. Chromatographic media which has been transported and/or stored in a vessel (450) must be prepared for packing in a chromatography column. The first step, on opening the container or vessel (450), is to remove the preservative supernatant from the media which reduces microbial contamination of the media. One example of such a preservative is ethanol or an ethanolic solution which is removed to lower the risk of flammability prior to use. This supernatant is removed by aspiration with the tubular member (410) by means of pump (444) through pressure hosing (451a-e) and valves (445a and 445b) to waste container (452). In FIG. 5, a removable filter unit (415) is shown positioned on one end of the tubular member (410), over the first orifice and second port, in order to prevent any particles of media being drawn into the tubular member during the decantation of storage liquid. The filter unit (415) is removed after aspiration. An appropriate buffer or water is then added from reservoir (454) through hosing (451c, b) and valves (445a, b and c) under pressure to break up any media aggregates in the vessel (450) and/or dilute the media to form a slurry therein. The buffer or water can be added to provide a final concentration of media of at least 10% weight to volume. Preferably the concentration of media is at least 50% weight to volume of buffer/water to allow direct packing of the column. This slurry is then aspirated through the tubular member (410) and circulated around the system via hosing (451a and b) and valves (445a, b and c) to be sprayed back into the vessel (450) under pressure. This repeating process of re-circulating, spraying and mixing the media under pressure breaks up any clumps or aggregates of media particles and produces an homogeneous mixture of chromatographic media. The process typically takes between 2 and 10 minutes to complete; at this time, the homogeneous mixture is aspirated from the vessel (450) by the tubular member (410) and transferred to a second vessel or slurry tank (453) in readiness for packing a chromatography column. Optionally, the media can be transferred directly to a chromatography column to effect packing thereof. If necessary, additional buffer or water from reservoir (454) can be used to rinse the walls of the vessel (450) to ensure complete transfer of media to the slurry tank (453).

It will be understood that while this process can be carried both manually and automatically under the control of an operator. The dotted line (457) indicates a media handling station which can be operated remotely by an operator or automatically under computer software control.

Figure 6:
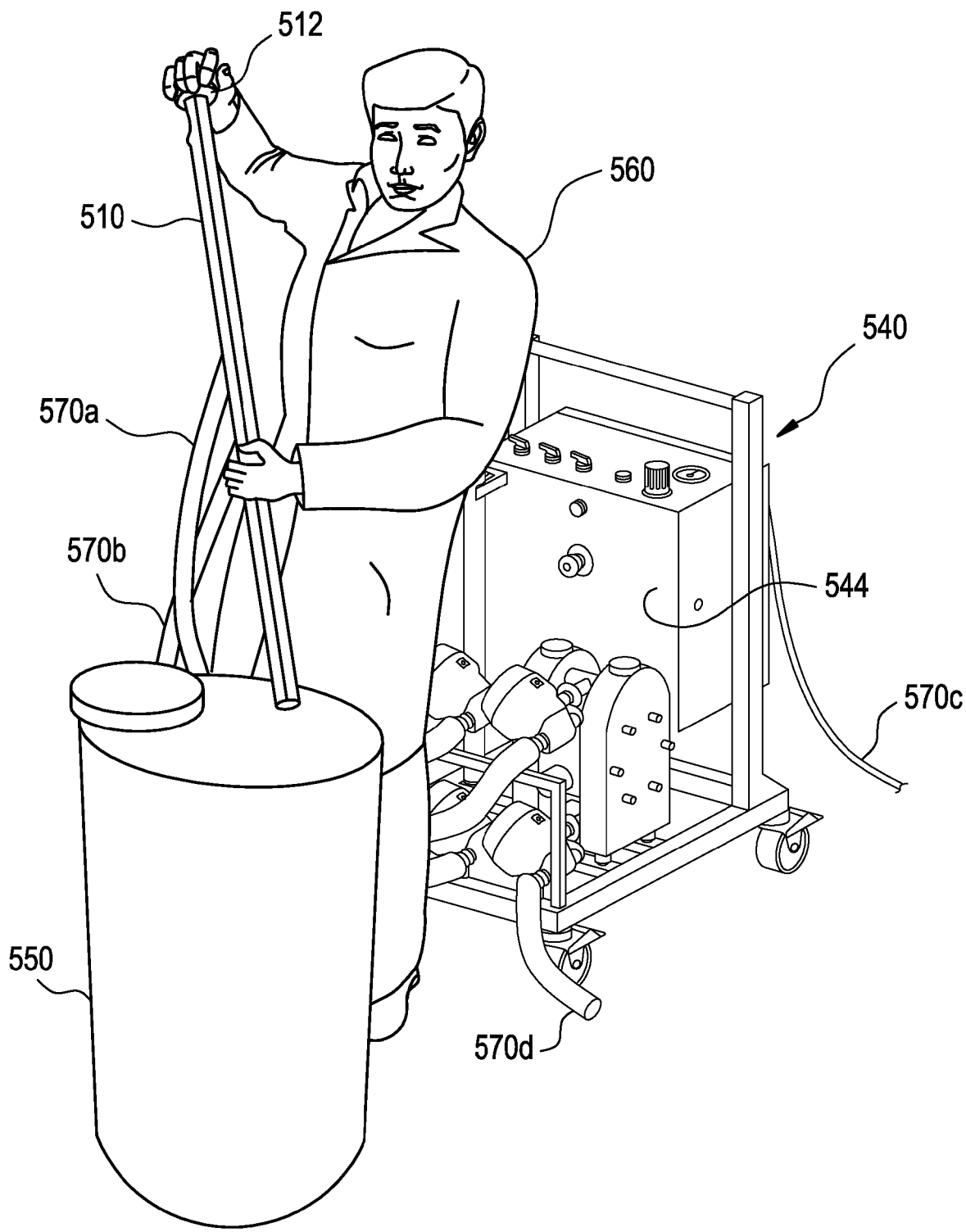
FIG. 6 shows an operator using the tubular member to form an homogeneous mixture of chromatographic media in accordance with the method of the invention.

FIG. 6 shows an operator (560) in the process of using the tubular member (510) to form an homogeneous mixture of chromatographic media which is stored within the container (550). In the figure, the tubular member (510) is connected to a pump (544) on a mobile pump skid (540) via pressure hosing (570a and b). The operator (560) will place the end of the member (510) into the media to aspirate the supernatant from the media and discard it as waste from hosing (570d).

Buffer or water will then be drawn from a reservoir (not shown) through hosing (570*c*) and sprayed into the media in the container/vessel. At the same time, slurry will be aspirated through the member (510) from the vessel to be circulated through the member (510) and the pump (544) and sprayed back into the container/vessel to facilitate mixing.

In the embodiment of FIG. 6, the tubular member can be separated into its component parts of first and second tubes to facilitate cleaning. These component parts are secured in position by a locking ring (512).

It is intended that the foregoing detailed description of the invention be regarded as illustrative rather than limiting and that it be understood that it is the following claims, including all equivalents, which are intended to define the scope of the invention.

What is claimed is:

1. An apparatus for forming a homogeneous mixture of chromatographic media in a vessel containing said media, the apparatus comprising:
   a tubular member (10), said member comprising a first tube (20) and a second tube (30) wherein,
   (a) said first tube (20) comprises an elongate body (21) having a first orifice (22) for entry of liquid or slurry therein and a second orifice (24) for exit of liquid/supernatant or slurry therefrom; and
   (b) said second tube (30) comprising an elongate body (31) having a first port (32) for entry of liquid or slurry therein and a second port (34) for exit of liquid or slurry therefrom, and wherein said tubular member is configured to simultaneously aspirate slurry from the vessel and spray the slurry back into the vessel to form said homogenous mixture of chromatographic media and wherein the apparatus is movable and the tubular member is a hand held rod.

2. The apparatus of claim 1, wherein the first tube (20) is concentric with said second tube (30).

3. The apparatus of claim 1, wherein the first tube additionally comprises a third orifice for insertion of said second tube therein.

4. The apparatus of claim 1, wherein the second tube is the inner tube and the first tube is the outer tube of the tubular member.

5. The apparatus of claim 1, additionally comprising a nozzle attached to said second port for exit of liquid or slurry therefrom.

6. The apparatus of claim 5, wherein said nozzle is disposed at an angle which is greater than or equal to 90 degrees to the elongate body of the second tube to prevent liquid or slurry being aspirated into the first orifice of the first tube.

7. The apparatus of claim 6, wherein the nozzle additionally comprises a flow diverter to produce said radial spray.

8. The apparatus of claim 1, wherein the first tube and the second tube are attached to each other by a releasable fixture to form the tubular member.

9. The apparatus of claim 8, wherein said releasable fixture is a locking ring.

10. The apparatus of claim 1, wherein said first tube and/or said second tube are composed of stainless steel.

11. The apparatus of claim 1, additionally comprising a removable filter unit (415) positionable over the first orifice (22) and second port (34).

* * * * *